United States Patent [19]

Sanders, III

[11] Patent Number: 4,846,802
[45] Date of Patent: * Jul. 11, 1989

[54] TAMPON APPLICATOR

[75] Inventor: Irl R. Sanders, III, Wilbraham, Mass.

[73] Assignee: Tambrands Inc., Lake Success, N.Y.

[ * ] Notice: The portion of the term of this patent subsequent to Feb. 23, 2005 has been disclaimed.

[21] Appl. No.: 60,832

[22] Filed: Jun. 12, 1987

Related U.S. Application Data

[63] Continuation-in-part of Ser. No. 879,140, Jun. 26, 1986, Pat. No. 4,726,805.

[51] Int. Cl.$^4$ .............................................. A61F 15/00
[52] U.S. Cl. ..................................................... 604/15
[58] Field of Search ....................... 604/11, 14, 15, 16, 604/18, 904

[56] References Cited

U.S. PATENT DOCUMENTS

| 2,222,088 | 11/1940 | Peterson | 128/263 |
|---|---|---|---|
| 2,450,138 | 10/1945 | Harwood | 128/263 |
| 2,829,646 | 8/1958 | Kurkjian | 128/263 |
| 2,832,342 | 4/1958 | Wingenroth | 128/263 |
| 3,058,469 | 10/1962 | Crockford | 128/285 |
| 3,059,641 | 10/1962 | Gershen | 128/263 |
| 3,059,642 | 10/1962 | Gershen | 128/263 |
| 3,090,385 | 5/1963 | Brecht | 128/263 |
| 3,101,713 | 8/1927 | Sargent | 128/263 |
| 3,103,929 | 9/1963 | Brecht | 128/263 |
| 3,115,876 | 12/1963 | Nalle | 128/263 |
| 3,135,262 | 6/1964 | Kobler et al. | 128/285 |
| 3,543,754 | 12/1970 | Jones | 128/263 |
| 3,674,029 | 7/1972 | Bates et al. | 128/285 |
| 3,759,258 | 9/1973 | Loyer | 128/263 |
| 3,766,921 | 10/1973 | Dulle | 128/263 |
| 4,048,998 | 9/1977 | Nigro | 128/263 |
| 4,077,409 | 3/1978 | Murray et al. | 604/904 |
| 4,269,187 | 5/1981 | Sakurai et al. | 128/263 |
| 4,273,125 | 6/1981 | Sakurai | 128/263 |
| 4,276,881 | 7/1981 | Lilaonitkul | 604/16 |
| 4,286,595 | 9/1981 | Ring | 128/263 |
| 4,329,991 | 5/1982 | Sakurai | 128/263 |
| 4,335,720 | 6/1982 | Glassman | 128/270 |
| 4,411,647 | 10/1983 | Sakurai et al. | 128/263 |
| 4,479,791 | 10/1984 | Sprague | 604/16 |
| 4,676,773 | 6/1987 | Shelton | 604/16 |
| 4,699,610 | 10/1987 | Hanano et al. | 604/16 |

FOREIGN PATENT DOCUMENTS

| 836423 | 1/1976 | Belgium . | |
| 782187 | 4/1968 | Canada . | |
| 944553 | 4/1949 | France . | |
| 2072411 | 9/1971 | France . | |
| 55-122724 | 12/1980 | Japan . | |
| 55-126822 | 12/1980 | Japan . | |
| 56-118621 | 12/1981 | Japan . | |
| 57-4259 | 12/1982 | Japan . | |
| 58-9129 | 12/1983 | Japan . | |
| 59-5920 | 12/1984 | Japan . | |
| 561173 | 5/1944 | United Kingdom . | |
| 577692 | 5/1946 | United Kingdom . | |
| 2033754 | 5/1980 | United Kingdom . | |
| 621893 | 5/1981 | United Kingdom | 604/15 |

Primary Examiner—C. Fred Rosenbaum
Assistant Examiner—Denise Whelton
Attorney, Agent, or Firm—Curtis, Morris & Safford

[57] ABSTRACT

A shortened tampon applicator of the telescoping tube type employs an ejector tube to store a tampon in its distal end and an outer tube disposed by a slip fit thereover to thus shorten the overall length of the tampon and applicator assembly. Directionally-locking inward flaps fixed within the distal end of said outer tube engage the distal end of the tampon stored in the ejector tube thus securing the latter relative to said outer tube while permitting only distal expulsion therefrom. The ejector tube preferably has inwardly biased flexible portions at its distal end which serve to catch behind the proximal end of the tampon. In the preferred version, the inwardly biased portions are unique undulations at the blunt distal end of the ejector tube which advantageously cooperatively functions with a tampon having an enlarged tail.

29 Claims, 6 Drawing Sheets

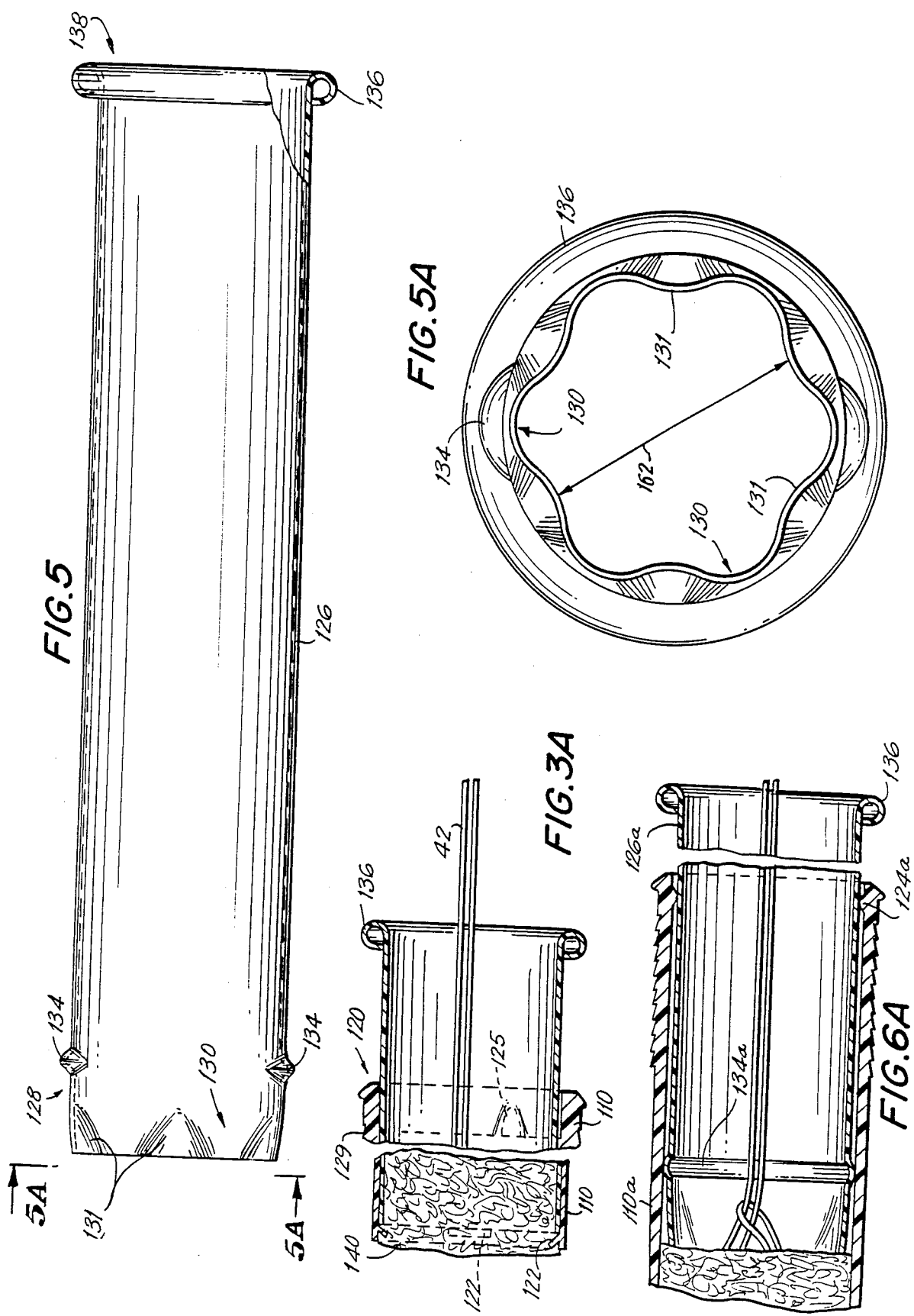

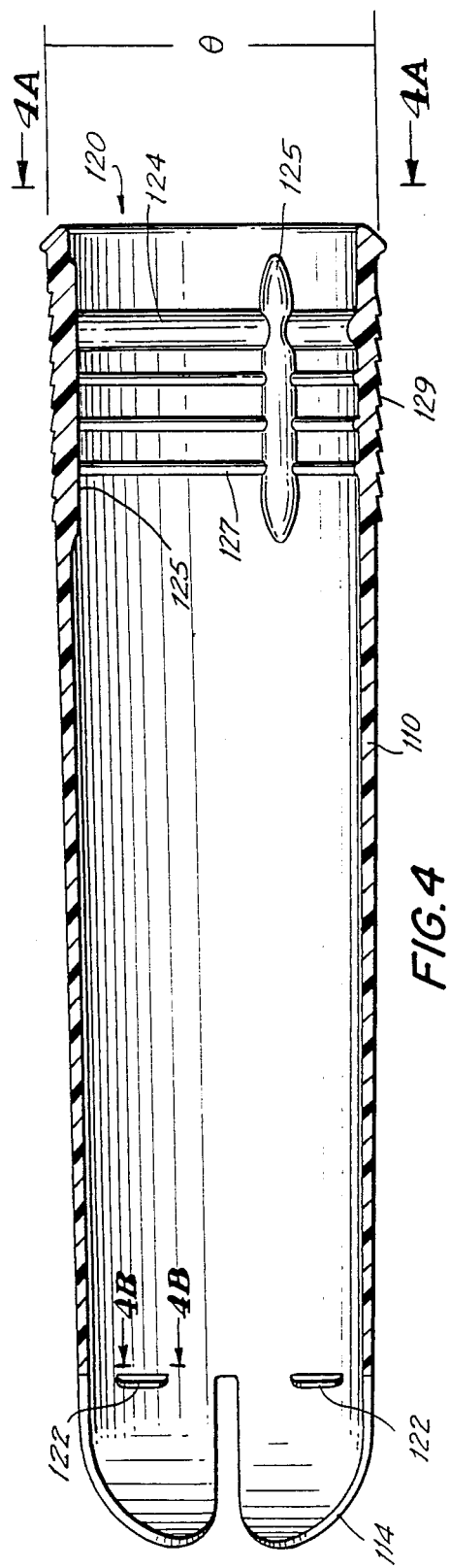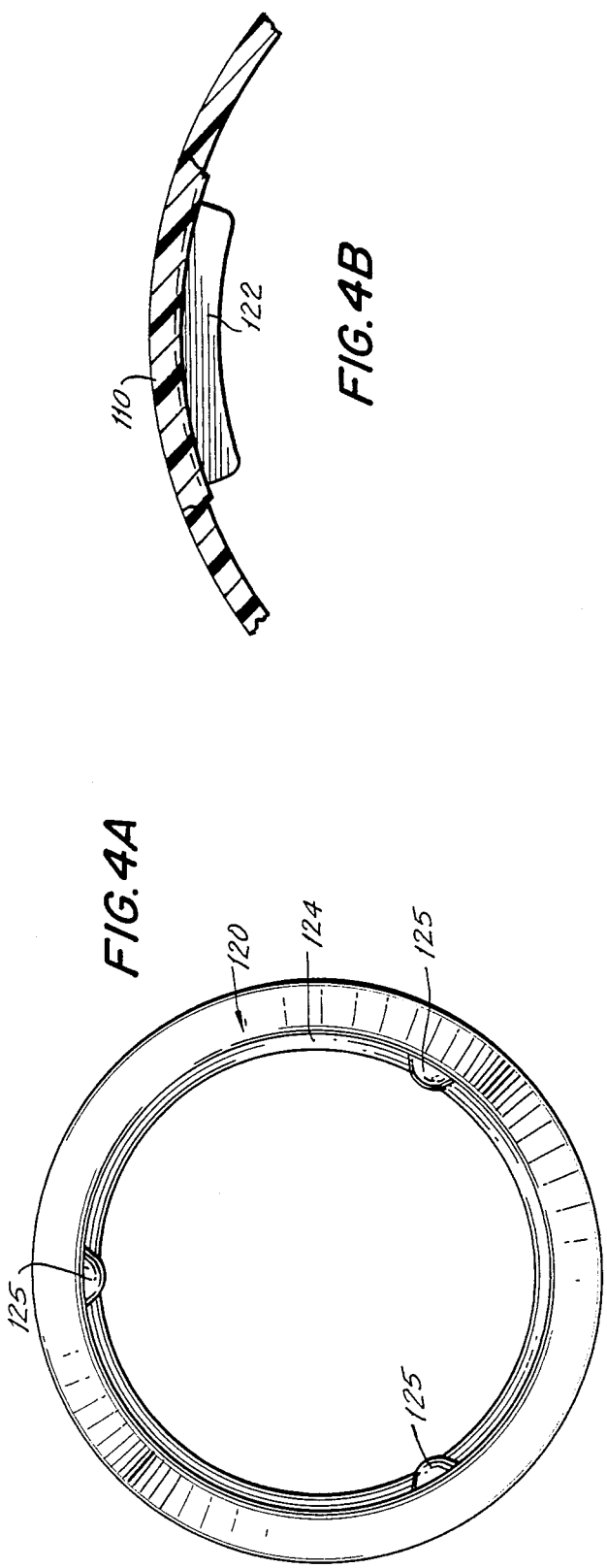

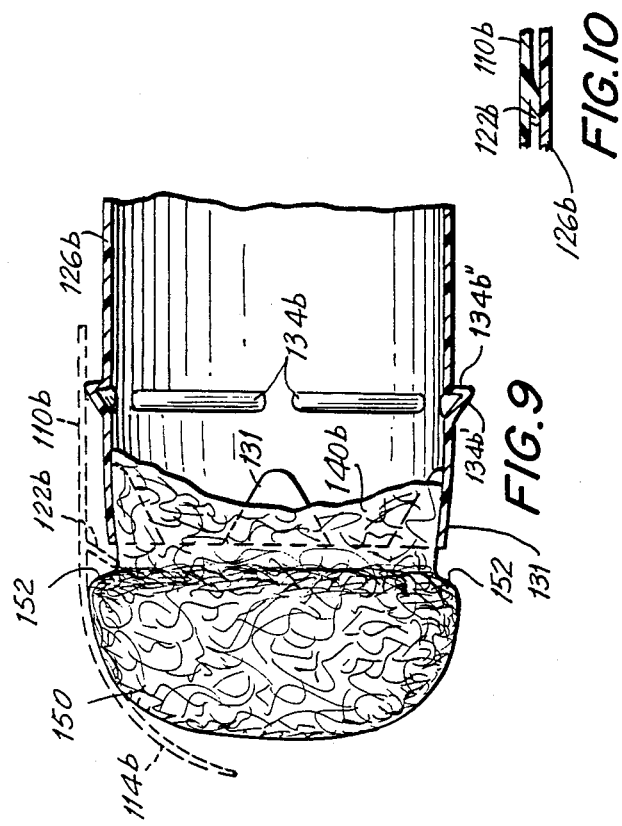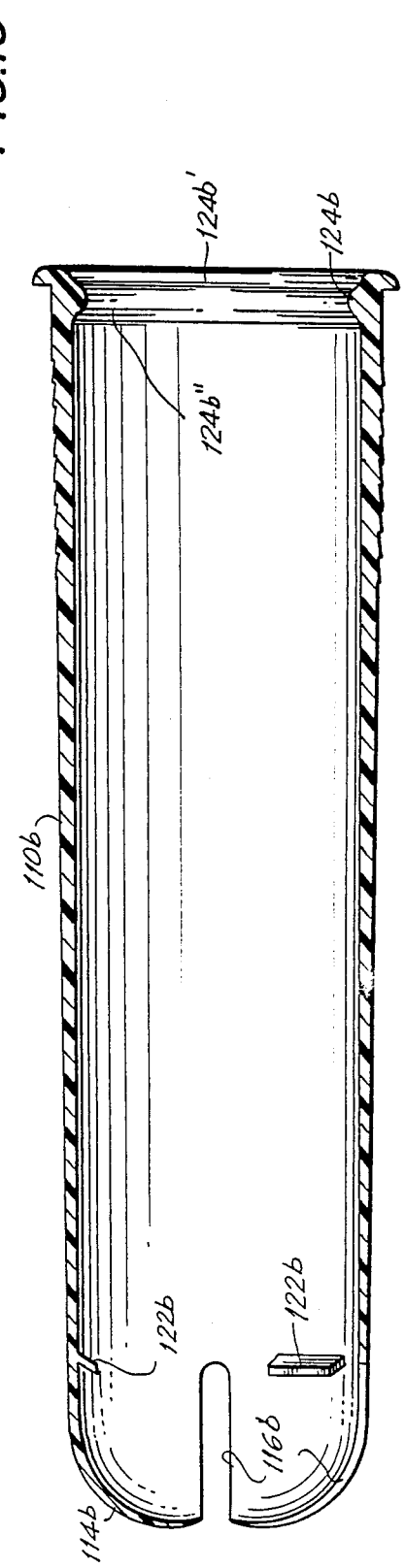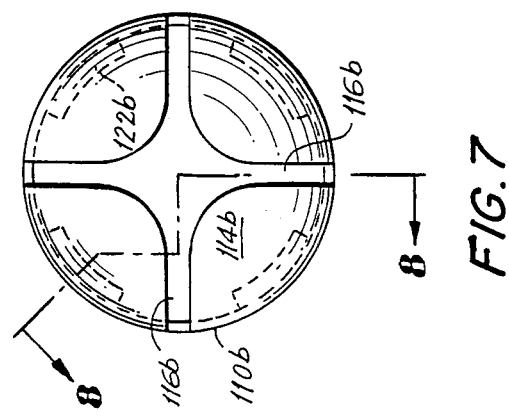

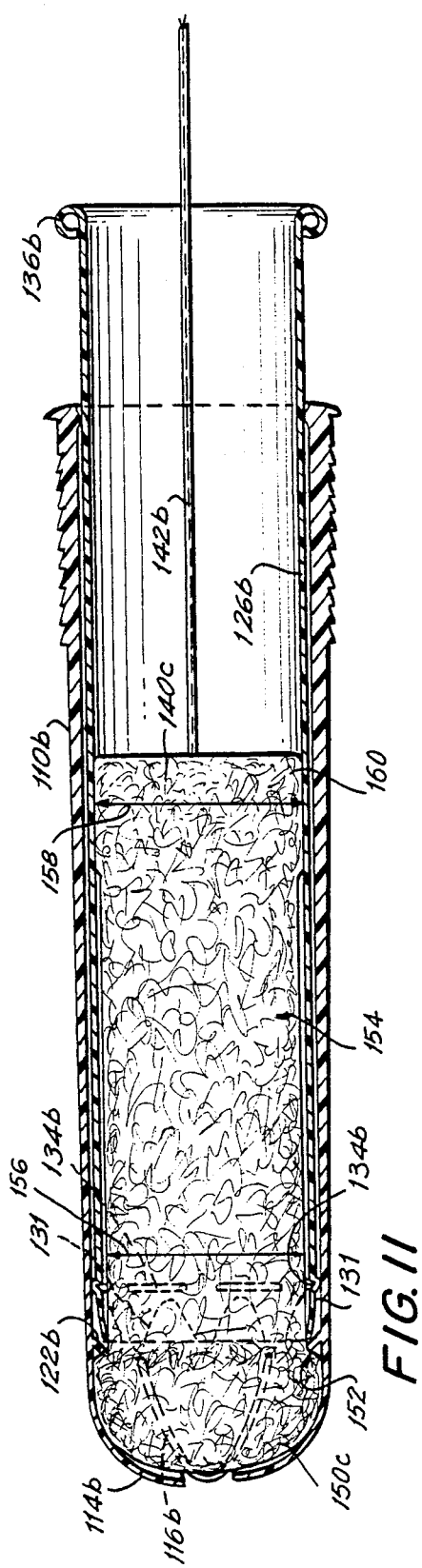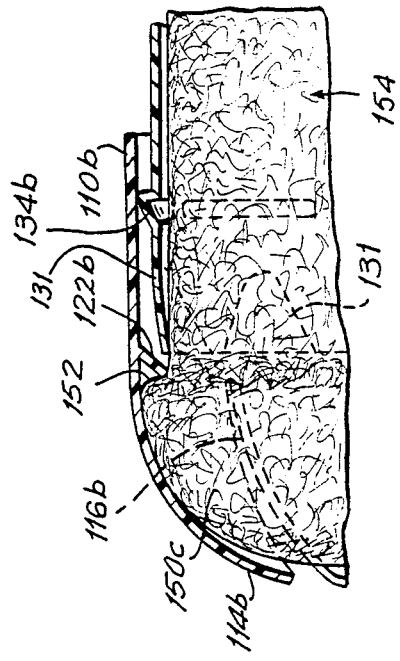

TAMPON APPLICATOR

This is a continuation-in-part application of application Ser. No. 879,140 filed June 26, 1986 now U.S. Pat. No. 4,726,805.

This invention relates to tampon applicators and, more particularly, is directed to tubular catamenial tampon applicators of the telescoping type.

BACKGROUND OF THE INVENTION

Most commercially available tampon applicators for introducing catamenial tampons intravaginally consist of a pair of telescoping tubes. The outer tube is designed to store a tampon at one end. The inner or ejector tube is slightly smaller in diameter and is slidably positioned behind the tampon carried in the outer tube. In use, the tampon is ejected from the applicator by pushing the inner tube into the outer tube to expel the tampon.

Several drawbacks are associated with such applicators for certain uses. For example, such tampon applicators are substantially longer than the tampons. First, the outer tube must be of length sufficient to assure proper depth of insertion. Next, when the tampon and outer tube are assembled with the ejector tube, a major portion of the latter tube necessarily extends out from the end of the outer tube. This results in the over-all length of the packaged ready-for-use tampon applicator being approximately two and one-half times the length of the tampon. As a result of such a relatively large size, the bulk and cost of the packaging for such applicators are increased.

Women commonly carry such packaged tampons (with applicators) in their purses. Because of the length of such applicators, they occupy a relatively large amount of space in the purse. It is therefore also desirable to produce a tampon applicator of smaller size which is less obtrusive. This is a particular problem for younger women who often prefer not to carry purses and with today's fashions often must use pockets in relatively tight-fitting clothes.

One type of tampon applicator which has been proposed to solve the above problems utilizes a substantially flat, elongated plunger arm which is stored positioned along the outside of and in longitudinal alignment with the outer tube. See U.S. Pat. Nos. 2,222,088; 3,059,641; 3,059,642; 3,103,929; 3,115,876; 3,424,159; 3,759,258; 3,831,605; and 4,269,187.

Another type of tampon applicator has been proposed to solve the foregoing problems by telescoping the ejector tube completely into the outer tube while storing the tampon in the distal end of the ejector tube. This also shortens the tampon and applicator assembly by the length of a tampon. Operatively, the ejector tube (often referred to as the pusher tube) is then drawn out most of the way from the proximal end of the outer tube leaving behind the tampon until the distal end of the ejector tube can engage the proximal end of the stored tampon. Each patentee discloses a different way of securing the stored tampon in the distal end of the outer tube to prevent proximal displacement of the tampon while the ejector tube is withdrawn therefrom. See U.S. Pat. No. 3,101,713; British patent No. 2,033,754; U.S. Pat. Nos. 2,832,342 (distal end of withdrawal string secured to slot in distal end of outer tube); 3,090,385 (having an ejector arm, rather than an ejector tube); 4,276,881; 4,286,595; and 4,479,791.

See also U.S. Pat. No. 4,411,647 where the ejector tube is conventionally stored in the proximal end of the outer tube, but the ejector tube is made in two separate parts which are stored prior to use with one telescoped over the other and are adapted to snap into a locked elongated postion prior to use.

Apparently, none of the foregoing types of applicators has ever been commercially successful.

OBJECTS AND SUMMARY OF THE INVENTION

Accordingly, it is an object of this invention to provide a tampon applicator that overcomes the above-described difficulties.

More particularly, it is an object of this invention to provide a commercially acceptable tampon applicator which is compact and of reduced size.

It is another object of this invention to provide a tampon applicator which is simple in construction and in manufacture and is convenient and easy to use.

It is a further object of this invention to provide a tampon applicator which permits the use of an ejector tube which is simple to assemble, without radial orientation problems, and can be made conventionally from paper or preferably from simple extruded plastic tubing, as opposed to being made less desirably by injection molding which requires more expensive machinery and generally results in undesirably thicker-walled tubing, and often gives mold parting-line imperfections on the product surface.

It is a still further object of this invention to provide a tampon applicator which can be handled and assembled in conventional type of machinery without the major machine redesign that would be needed if radial orientation between the outer tube and the ejector tube were required.

In accordance with a preferred embodiment of this invention, a tampon applicator includes an ejector tube adapted to store a tampon therein. An outer tube is slidably disposed over the ejector tube. The outer tube is adapted to pass the tampon through its distal end during an ejection operation. Directionally locking inwardly-projecting flaps are circumferentially affixed at or near the inner distal end of the outer tube for engaging the distal end of a tampon which is stored in the distal end of an ejector tube, which in turn is telescopically positioned in the outer tube. These flaps function so as to prevent movement of the tampon in the proximal direction. Preferably, the flaps abut the distal end of the ejector tube. Despite the surprisingly small and relatively fragile size, and circumferential shape and placement of these flaps, they are unexpectedly effective even very close to the distal ends of the tampon and of the outer tube. Thus, when the ejector tube is partially withdrawn from the outer tube so as to be positioned behind the tampon, the flaps are effective to fix the tampon relative to the outer tube. However, when the ejector tube is forced distally back through the outer tube so as to eject the tampon therefrom, the flaps permit the forward displacement and expulsion of the tampon.

The outer tube advantageously has petals at its distal end. Preferably, the ejector tube is formed with resilient circumferential undulations at its distal end. These are urged outward when a tampon is pushed into the ejector tube through the proximal end, i.e., during manufacture. When used by the ultimate consumer, the ejector tube is partially proximally withdrawn from the outer tube to a "cocked" position with the applicator ready for vaginal insertion of the tampon, and the distal end of the ejector tube is thus disposed behind the tampon so that these undulations are free to close in behind the tampon and engage the proximal end of the latter.

The undulations should not be set inwardly too much. Otherwise, they might grip rather than slide over the tampon during the proximal withdrawal of the ejector tube and (1) thus undesirably stretch the compressed tampon longitudinally and (2) consequently also still grip the tampon at the end of the proximal withdrawal (thus preventing the ejector tube from expelling the tampon by the subsequent distal stroke of the ejector tube).

The crimped flutes, which form the undulations set in the proximal end of the plastic ejector tube, can be subject to loss of shape due to plastic creep. This can result from prolonged storage of the tampon and applicator assembly, where the undulations are flattened between the stored tampon and the outer tube. With such memory loss in the plastic due to creep, the undulations may not close inwardly sufficiently behind the tampon when the ejector tube is withdrawn into the cocked position. This can result in the tampon slipping at least partially back into the ejector tube during the distal pushing stroke of the ejector tube, resulting in at least incomplete expulsion of tampon. The applicant has successfully overcome this and other problems by the surprising expedient of having the tampon diameter 0.005 to 0.030" smaller at the shoulder adjacent its distal head end relative to its proximal tail end.

Conversely, certain kinds of tampons may be made from a sufficiently springy material, such that the undulations may not be needed at all. In such a case, the thickness of the ejector tube may be sufficient to engage the proximal end of the tampon effectively to assure reliable expulsion.

Less desirably, the ejector tube may have fingers at its distal end; however, these preferably are short and relatively stiff and are adapted to slide over the tampon upon withdrawal of the ejector tube and automatically to close inwardly behind the tampon sufficiently to engage the end of the latter.

The outer tube may preferably be injection molded of plastic synthetic resin. The ejector tube may optionally be so molded.

In this specification and the accompanying drawings, I have shown and described a preferred embodiment of my invention and have suggested various alternatives and modifications thereof, but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it and embody it in a variety of forms, each as may be best suited to the conditions of a particular use.

BRIEF DESCRIPTION OF THE DRAWINGS

FIG. 3A is a detail of a view similar to FIG. 3 of an alternative preferred embodiment showing a tampon and applicator assembly where the outer tube has no petal sections at its distal end;

FIG. 4 is a longitudinally sectioned view of the outer tube portion of the embodiment of FIG. 3;

FIG. 4A is an end view of the proximal end of the tube of FIG. 4;

FIG. 4B is a sectional view taken at line 4B—4B of a portion of the distal end of the tube of FIG. 4;

FIG. 5 is an elevational side view (partially-sectioned) of the ejector tube of the embodiment of FIG. 3;

FIG. 5A is an end view of the distal end of the ejector tube of FIG. 5;

FIG. 6A is a detail of an embodiment similar to FIG. 6 but modified such that the tube restraining means are changed to a fully circumferentially-extending detent ring axially overlapping a similar single stopping ring, which are respectively formed on the outer distal end of the ejector tube and the inner proximal end of the outer tube;

FIG. 7 is a distal end elevational view of a still further modified preferred embodiment of an outer tube similar to that shown in FIG. 6A;

FIG. 8 is a longitudinally sectioned view taken on angled line 8—8 of the outer tube shown in FIG. 7;

FIG. 9 is a longitudinally sectioned view of the distal end of the ejector tube for the applicator embodiment shown in FIGS. 7 and 8 containing a modified compression-hardened tampon having an enlarged head, a portion of the outer tube from FIG. 8 is shown in dotted outline;

FIG. 10 is an enlarged sectional detail of certain structures of FIG. 9, but relatively shifted to the expelling position (showing a flap flattened to permit the ejector tube to pass thereby);

FIG. 11 is a longitudinally sectioned view of the applicator embodiment shown in FIGS. 7 to 10 containing a further modified tampon having a smaller diameter body with an enlarged head and a slightly enlarged tail; and FIG. 12 shows an enlarged portion of FIG. 11, better showing the small clearance between the tampon and the ejector tube at the shoulder area of the tampon.

DESCRIPTION OF COMMON ASSIGNEE'S EARLIER DEVELOPMENT

Figure 1:
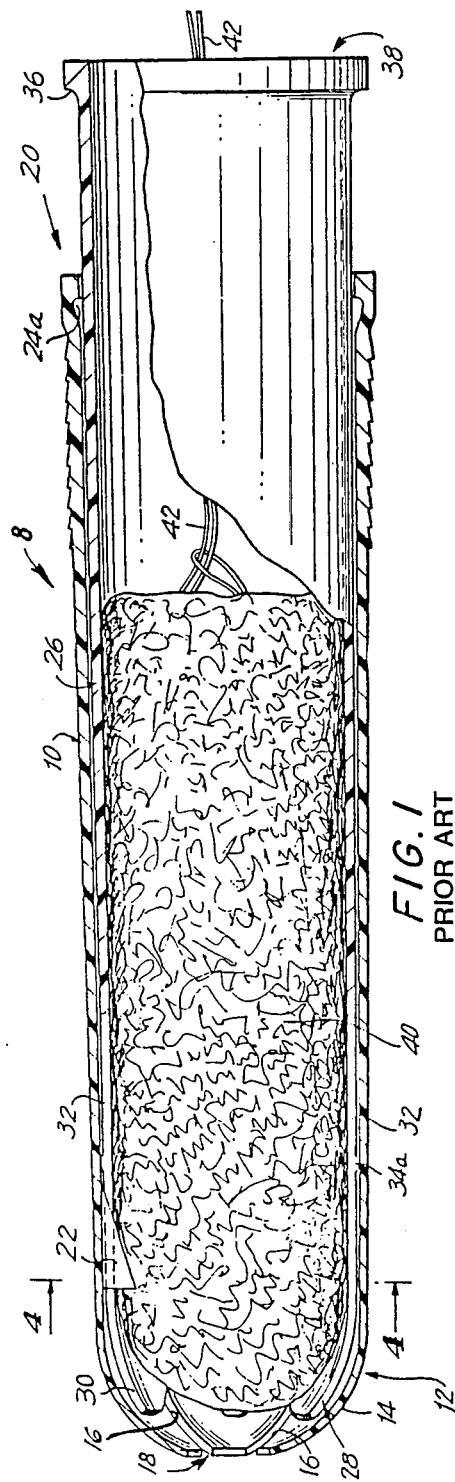
FIG. 1 is a partially sectioned longitudinal view of a prior art tampon applicator according to assignee's U.S. Pat. No. 4,479,791.
Figure 2:
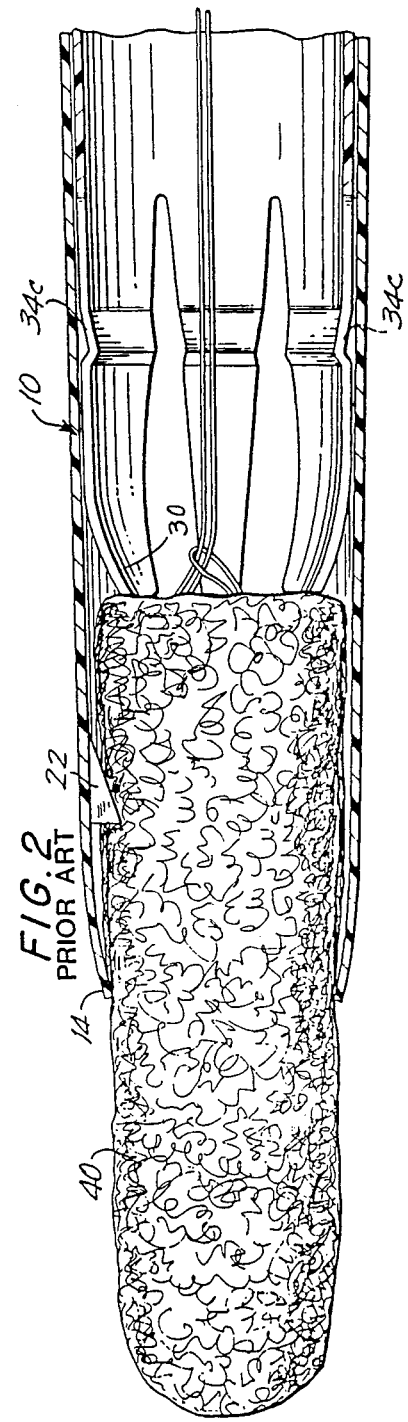
FIG. 2 is a longitudinally sectioned view of the tampon applicator of FIG. 1, (but with an alternative embodiment of a portion of the restraining means 34c), showing the fingers of the ejector tube expelling the tampon from the outer tube.

FIGS. 1 and 2 illustrate embodiments of the tampon applicator 8 of U.S. Pat. No. 4,479,791 (incorporated herein by reference), of which the present invention is a surprisingly simplified and effective improvement.

The cylindrical outer tube 10 has at its distal end 12 conventional petal sections 14 which are separated from each other by respective slots 16. The petal sections 14 are made relatively flexible and are normally biased in a substantially arcuate closed configuration to form a rounded tip having a central opening 18 at the distal end 12. This rounded shape of the distal end 12 helps facilitate the insertion of the applicator into the vaginal cavity. Such outer tubes 10 are preferably constructed from any suitable smooth plastic material. The opposite or proximal end 20 of the outer tube 10 is open.

The outer tube 10 further includes an unconventional plurality of inward projections 22 formed along an inner circumferential portion thereof. These projections 22 are of a substantially flat, right triangular configuration with the long side thereof extending at an acute angle from the inner wall of the outer tube 10 towards the central opening 18. The projections 22 extend inwardly from the outer tube 10 sufficiently to engage a catamenial tampon 40 disposed therein. Unless made quite wide, these axially extending projections 22 may have a tendency to roll over and become inoperative, especially, if the tampon has a relatively hard surface from a high degree of compression. The outer tube 10 as shown in FIG. 1 includes an annular groove 24a along an inner circumferential portion of the proximal end 20.

The tampon applicator 8 illustrated in FIG. 1 further comprises an inner or ejector tube 26. This serves as a hollow plunger for ejecting a tampon 40 positioned within the distal end of the outer tube 10. The ejector tube 26 is dimensioned to slidably move within the outer tube 10, with minimal clearance therebetween. The ejector tube 26 is also preferably slightly longer than the outer tube 10 to assure complete ejection and proper depth of placement of the tampon 40. Being hollow, the ejector tube also permits proper placement of the withdrawal string 42. The distal end 28 of the ejector tube 26 is formed with a plurality of fingers 30 which are separated from each other by slots or openings 32 through which the projections 22 of the outer tube 10 extend to engage the tampon 40 disposed therein. In the same manner as with petal sections 14 of the outer tube 10, the fingers 30 are made so as to be slightly biased towards a closed configuration, as shown in FIGS. 1 and 2.

In order to limit the axial movement of the inner tube 26 relative to the outer tube 10, each such finger 30 further includes a raised detent or rib 34a to coact with the groove 24a as a restraining means. The placement of these can be reversed (for example, see groove 34c in FIG. 2 which would coact with a corresponding rib 24c [not illustrated]). The ejector tube 26 also includes an outwardly directed circumferential retention flange 36 at its proximal end 38.

DETAILED DESCRIPTION OF PREFERRED EMBODIMENTS OF THE INVENTION

A preferred embodiment of the applicator assembly 108 incorporating the principles of this invention is shown in FIGS. 3 to 10.

Elements in this embodiment, which are identical with those in the illustrated prior art device shown in FIGS. 1 and 2, are identified with the same reference numbers. Analogous structural features in this embodiment are identified with the same reference numbers, but raised by 100.

Figure 3:
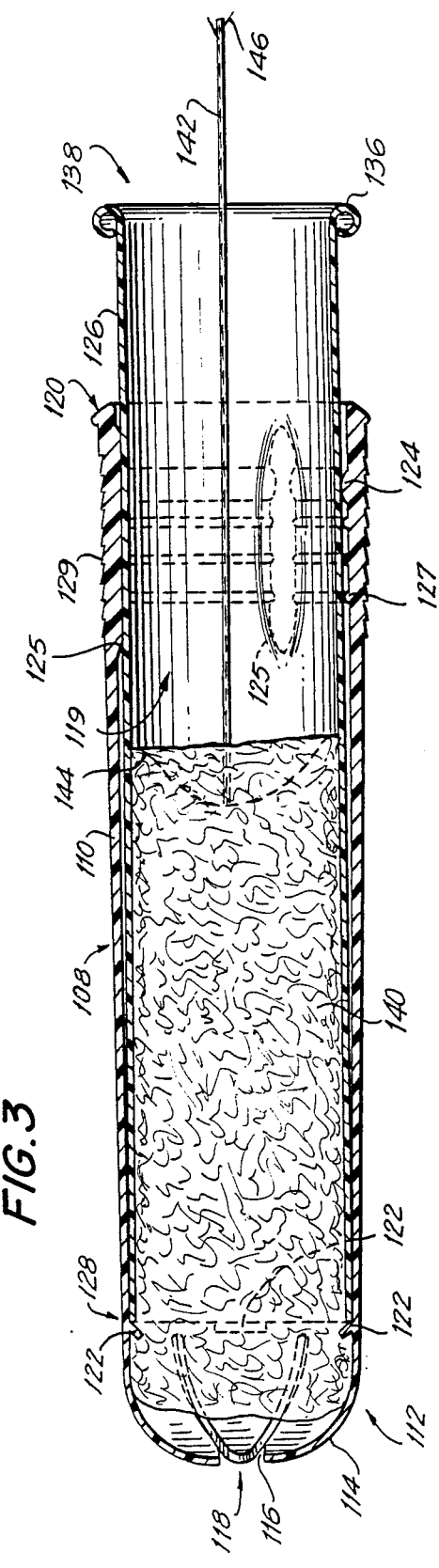
FIG. 3 is a longitudinally sectioned view of a preferred embodiment of a tampon applicator according to the present invention.

In the embodiment of FIG. 3, a cylindrical outer tube 110 (FIG. 4) has at its distal end 112 a plurality of petal sections 114 defined by slots 116, and converging to a central opening 118. The tampon 140 is stored in the distal portion of the central cavity 119 of the tube 110, and is held in place by one or more flaps 122 (shown in FIG. 4B, see also FIGS. 7 and 8). Preferably, four such flaps 122 are provided, one disposed approximately at the base of each respective petal section 114.

These flaps 122 are disposed in an inward direction generally perpendicular to the axis of the outer tube 110 and are preferably canted towards the distal discharge end thereof.

An optional outer ridged or knurled finger gripping surface 129 at the proximal end of the tube 110 provides the user with a secure finger grip of the outer tube 110.

As shown in FIGS. 3 and 5, the inner pusher or ejector tube 126 is disposed within the outer tube 110 and over the stored tampon 140. The distal end 128 of the tube 126 preferably abuts the flaps 122 in the stored position (FIG. 3). As shown in FIGS. 5 and 5A, the distal end 128 is preferably provided with a plurality of undulations 130 (e.g., six).

Figure 6:
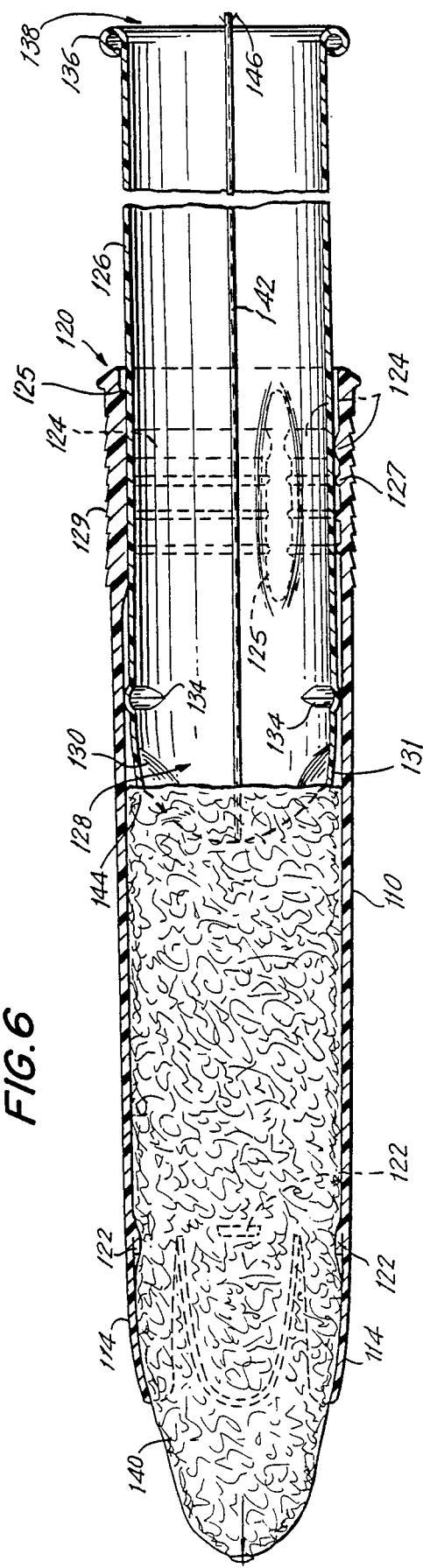
FIG. 6 is a longitudinally sectioned view of the embodiment of FIG. 3 showing the ejector tube pushing a tampon out the distal end of the outer tube.

The undulations 130 are resiliently flexible, so that in the stored position, as shown in FIG. 3, the inner portions 131 of the undulations 130 are biased flexibly outward by the carried tampon 140. This permits the undulations 130, and the remainder of the tube 126, to pass over the tampon 140 that is secured in the outer tube 110 by the flaps 122, during partial withdrawal of the ejector tube 126. Then, because of the stiff flexibility of the undulations 130, when the ejector 126 is sufficiently withdrawn as shown in FIG. 6, at least the inwardly directed portions 131 of these undulations 130 will flex inwardly to a lesser diameter 162 than that of the tampon 140. Consequently, when the discharge tube 126 is moved forwardly, i.e. in the distal direction, the tampon 140 will be engaged at its proximal end by undulations 130, and thus urged out the distal discharge end 112 of the outer tube 110.

As shown in FIGS. 3 and 6, the distal or base end of the tampon 140 may be uniquely formed with a concave configuration leaving a more dense center and a relatively softer peripheral ridge 144. The softer ridge 144 aids the proximal end of the tampon 140 in catching on the undulations 130, thus serving as an unidirectional lock to prevent the tampon 140 from re-entering the ejector tube 126 during expulsion.

Applicant has discovered that an even more reliable and effective alternative to enhance the function of the undulations 130 is accomplished by use of a two-diameter (or equivalent) tampon, see FIG. 11. Because the compressed tampon is stored inside the inner ejector tube 126, it displaces (forces outwardly) the crimped flutes 131 (undulations) in the distal end of the plastic ejector tube 126 flattening the flutes 131 against the inner surface of the outer tube 110. Over a period of time under this force the plastic relaxes (creeps) such that the flutes 131 will not spring back to their original (preassembled) minimum inside diameter 162 after the inner ejector tube 126 is withdrawn from around the tampon 140.

If the resulting minimum inside diameter is too large, the tampon 140 can be at least partially forced back inside of the ejector tube 126 during the expulsion stage, which can cause functional difficulties or failure (by incomplete expulsion, improper positioning, or the like).

The two-diameter tampon 140c shown in FIGS. 11 and 12 reduces the amount of creep by reducing the diameter of the tampon 140c at least in the area of the contact points between the ends of the flutes 131 and the body of the stored tampon 140c. In the preferred embodiment, this provides a differential of the tampon shoulder inner diameter 156 (i.e. the accommodation diameter) to the tampon tail diameter 158 such that the net effect of any creep is reduced, thus ensuring reliable operation. In other words, the minimum inside diameter 162 (See FIG. 5A) of the flute ends of the ejector tube 126b when in the cocked position is effectively less than the diameter 158 of the tampon tail 160. This assures positive engagement of the undulations 131 against the proximal tail end of the tampon 140c during the expulsion step. Advantageously, the accommodation diameter 156 remains constant along the major portion of the tampon body 154. This reduces strain on the flaps 122b. However, the transition from the accommodation diameter 156 to the large tail diameter 158 can be sloped, etc. (so the two-diameter shape per se is not critical).

Preferably, the diameter 162 of the tampon 140c at its tail 160 (the proximal end) approximates the inside diameter of the ejector tube 126b.

The ejector tube 126 can be functional even without undulations 130, or the like, if the tampon 140 is sufficiently expansive to fit closely within the outer tube to ensure positive engagement by the unmodified distal end of the ejector tube against the proximal end of the tampon during the ejection step.

Alternatively, in the broader aspects of this invention the distal end 128 of the ejector tube 126 can have fingers (not shown) similar to the fingers 30 of tube 26, but preferably, shorter so as to give a stronger structure. However, normally, the aforementioned disadvantages of such fingers could outweigh any minor increase in length of the ejector tube (or alternatively, shortened length of the assembled applicator tubes) which might be achieved by the use of such fingers 130.

The outer tube 110 is preferably tapered at a small angle $\theta$ (see FIG. 4) towards the distal discharge end of the tube 110. This facilitates removal of the formed tube 110 from the molding apparatus.

FIGS. 4 and 4A also show one type of restraining means previously developed by applicant's assignee. A stopping ring 124 is provided on the inner surface of the outer tube 110 near the proximal end thereof. A plurality of detents 134, preferably two (see FIGS. 5 and 5A) to six (see FIG. 9), are circumferentially aligned and extend radially outwardly from the ejector tube 126 near its distal end 128. The ring 124 instead of being a continuous ring, could also be made of a plurality of circumferentially aligned segments.

These two members 124 and 134 act together as the restraining means to reduce the chance of complete withdrawal of the inner ejector tube 126 from the proximal end 120 of the outer tube 110 during the proximal movement of the ejector tube 126 prior to the discharge of the tampon 140.

Longitudinal ribs 125 and annular ribs 127 may also be provided on the interior of the proximal end of the outer tube 110. These help compensate for the taper in the outer tube and to give a better fit between tubes 110 and 126.

An alternative more preferred, unidirectional, restraining means is illustrated in FIGS. 8 and 9. In this latter preferred means, the six raised detents 134b each have in one direction an angled sloping face 134b' (for example, 60° to the axis) and a perpendicular face 134b'' in the other direction (to permit easy initial assembly and yet to prevent disassembly). In the preferred stopping means, the ribs 125 and 127 are omitted, leaving only ring 124b on the inner wall of the outer tube 110b. This has an inner slope 124b'' relative to the longitudinal axis of about 35° to permit withdrawal from the mold in which it was formed. Otherwise, a more perpendicular slope would be appropriate. The opposing slope 124b' approximates 45° to 50°.

A more conventional restraining means can also be used, as shown in FIG. 6A, where the detents 134 are replaced by a single complete circumferential raised detent ring 134a. The stopping ring 124a and the raised detent rib 134a are rounded (without the more positive locking perpendicular face 134b''); however, they similarly axially overlap to inhibit disassembly of the tubes 110a and 126a.

At its proximal end 120, the tube 126 is rolled outwardly to form an annulus 136, serving as a retension flange.

The flaps 122 engage the forward, or distal portion of the tampon 140 and prevent its proximal movement when the ejector tube 126 is partially withdrawn. However, as shown in FIG. 6, these flaps 122, preferably, are distally inclined and as such tend to securely grip a tampon against proximal movement (much the way a speed nut functions, making a uni-directional jamming engagement) Yet these flaps 122 bend (distally) out of the way when the ejector tube 126, and the carried tampon 140, are moved distally (during assembly and during customer use), thereby aiding the unidirectional free movement of the tampon 140. Compare the flaps 122 in FIGS. 3 and 6; see also flaps 122b in FIG. 10.

The unique and unexpected effectiveness of the flaps 122 can best be appreciated by comparison to the prior art illustrated in FIGS. 1 and 2. The prior art projections 22 are shown as longitudinally-extending broadly-based pointed wedges. These are shaped and placed to extend towards the proximal end. They are not canted nor are they flexible in the axial direction. They require that the ejector tube 26 have elongated fingers 20 (so as to pass clear of the wedges during the expulsion operation and also during assembly and to avoid undesirably increasing the overall length of the stored tampon and applicator assembly). However, as most dramatically shown in FIGS. 3A and 8, applicant preferably uses circumferentially extending flaps, which eliminates the need for fingers. These circumferentially-extending flaps are unexpectedly effective not only in engaging the tampon 40 advantageously almost at its very distal end, but also, doing so with a structure having a minimal longitudinal and radial extent. This permits the use of an ejector tube 126 which can be blunt ended (i.e. no finger slots 32).

This elimination of fingers 30 gives several significant advantages. An ejector tube 26 with fingers 30 must be rotated for axial alignment of the slots 32 with the projections 22, requiring more complicated and expensive assembly machinery. Even with such machinery, the manufacturing reliability is probably decreased, increasing risk of quality control problems The ejector tube 26 with curved fingers 30, as a practical matter probably must also be made by injection molding (and not from wound paper or simple extruded plastic tubing), resulting in a heavier and more expensive product. The taper usually required on a molded tube for release from the mold complicates the maintenance of a proper fit between the telescoping tubes 10 and 26. If a taper is not used, then an undesirable parting line typically would be needed (which is abrasive and unsightly to the user). Further, molded ejector tube 26 would be expected to have thicker walls, and thus cumulatively, result in a marked increase in wall diameter of the outer tube (possibly, 0.05" or more, when allowing for increased thickness and required clearance). Additionally, there is the need for the fingers 30 to be adequately beefed-up to have sufficient rigidity and strength to expel the tampon consistently, especially, to achieve inward flexing without deforming under expulsion pressure.

Tampons come usually in three traditional sizes; regular, super, and super plus. In a typical plastic applicator embodying the present invention, the "super" size advantageously will have dimensions as described below. The molded outer tube 110 at its distal end has an inner radius of about 0.3" and a wall thickness of about 0.02". The four flaps 122 subtend an axial angle of about 40° (and would thus be approximately 0.2" transversely), are about 0.015" thick axially, extend radially inwardly about 0.04" from the tube 110, and are canted distally at a 60° angle to the axis thereof. Thus the linear tip portion (in the free end) of the flap 122 is oriented distally relative to the base portion (i.e. the end where the flap joins the outer tube 110). The extruded plastic ejector tube 126 has a constant outside radius of about 0.28" and a wall thickness of between 0.01-0.02". Thus, the flaps 122 might, typically, extend only about 0.02" into the tampon 140 stored within the end of the ejector tube 126, and yet, these reliably secure the tampon 140 relative to the tube 110 during proximal withdrawal of the tube 126. From this, it can be seen that the flaps 122 in fact can be made to extend radially inward only little more than the thickness of the ejector tube 126. Yet, this is adequate unidirectionally to hold the tampon.

Sometimes, tampons which are highly compressed while dry form a relatively hard surface. This would typically occur occasionally only in the smaller size "regular" tampons. It may be difficult sometimes for flaps 122 to grip reliably in all cases into such a surface. In such circumstances, the tampon 140b may preferably be formed with a slight head 150 at the distal end to provide an abrupt shoulder 152. As shown in FIG. 9, this shoulder 152 provides a positive catching point for the flap 122b to bear against so as to resist proximal withdrawal of the tampon 140b. See also FIGS. 11 and 12.

As a further feature, the tampon head 150 is advantageously formed with a rounded shape to closely underlie the soft smooth petals 114b of the outer tube 110b to give adequate support to the petals to prevent the user from being pinched in the slots 116b, see FIGS. 7 to 12. The tampon head 150 can achieve this purpose without extending to the very end of the petal tips (thus leaving room for a slight longitudinal expansion of the stored tampon). If the tampon head is not needed to support the petals 114b, then it can be quite short longitudinally (just enough to give substance to the shoulder 152), see for example the dimensions shown in FIG. 3A (where no petals are used).

For an applicator of these general dimensions, the transverse dimension of the flaps 122 range from about 1/16 to ¼", and preferably, range from ⅛ to 3/16". Any more than ¼" would tend to reduce flexibility and tend to increase the resistance to expulsion of the tampon. However, within the broader aspects of this invention, the flaps 122 could be a single 360° flap, either continuous or slit at discrete intervals to form a series of closely spaced or abutting flaps.

The size, shape, placement and number of flaps can be varied, as can the flexibility, the material used for construction, and angle of distal canting; so long as the desired function of unidirectional securing of the tampon is achieved. However, in order to obtain the advantages of this invention, the flaps must be dimensionally greater in the circumferentially transverse direction than in the axial direction. They preferably should be essentially closely adjacent to the circumferentially continuous portion of the distal end 112 of the outer tube 110 and advantageously, should be essentially in circumferential alignment with one another. Without such alignment, then to keep the same overall assembled length, the ejector tube 126 would become somewhat unnecessarily shortened. Preferably, an inscribed circle tangentially touching the tip of each canted flap (in the absence of a tampon) would have a diameter slightly smaller than the diameter of the stored tampon at the points of contact between the flaps and the tampon.

The petal sections 114, with the slots 116, make that portion of the distal end 112 of the outer tube 110 circumferentially discontinuous. If the flaps 122 are positioned right at the base of the petal sections 114, they can still function reliably, but if positioned much further out on the sections 114, then the flexibility of the sections 114 would hamper the effectiveness of the flaps 122 by permitting the flaps to swing free of the tampon 140 with which they are designed to coact. The curvilinear aspect of blade-shaped flaps 122 with the two relatively pointed corners (as best shown in FIG. 4B) serves to aid in the effectiveness of the flaps. The inner "blade" edge of the flaps could advantageously be serrated, if an increased unidirectional grip were deemed necessary for a particular tampon.

Referring to one preferred embodiment in FIG. 3, the assembled tampon-and-applicator 108 is shown ready for packaging, with the ejector tube 126 being substantially within the outer tube 110. See a similar, more preferred embodiment in FIG. 11. A tampon 140 is stored within the ejector tube 126, not directly in the outer tube. The tampon is comprised of an absorbent material formed into the general shape of an elongated cylinder and having attached to its rearward portion a withdrawal string 142, as is conventional in the art. The withdrawal string 42 in the prior art in FIGS. 1 and 2 is shown doubled to form a loop locking the two loose ends. It is shown in FIGS. 3 and 6 as a single string 142 sewn to the tampon pad by thread 146. The outer tube 110 is telescoped over the ejector tube 126 so that the distal ends 126, 128 of the two tubes 110, 126 are closely adjacent to one another. It is thus readily apparent from FIG. 3 that the dimension of the tampon applicator 108 in that illustrated preferred embodiment in its stored configuration is approximately 1.8 times the length of tampon 140 in contradistinction to previously-described conventional commercial telescoping tube applicators having a length of two and one-half times that of the tampon stored therein. The length of the improved applicator is now controlled primarily by the insertion depth desired (which determines the length of the outer tube) rather than by the applicator design requirements. Note that where a tampon has been compressed longitudinally as well as transversely, it is typical that there is provided some allowance for longitudinal elongation (due to absorption of ambient moisture while stored in the applicator).

In operation, outer tube 110 is firmly held at the finger grip area 129 while ejector tube 126 is partially withdrawn therefrom (i.e. ejector tube 126 is axially moved in the proximal direction away from central opening 118). During this activating step, the tampon 140 remains in a fixed position relative to outer tube 110 by means of the flaps 122 which grip the tampon and restrain its movement in the proximal direction. The undulations 130 of the ejector tube 126 slide over the tampon 140. Once the undulations 130 are withdrawn past the proximal or rear end of the tampon 140, portions 131 close towards each other so as to be positioned behind the tampon 140 for the start of the ejection operation (see FIG. 6).

The tubes 110 and 126 of the applicator are prevented from becoming disassembled during the activating or cocking step by a restraining means 124 and 134.

After the ejector tube 126 has been pulled out to its operative position, the outer tube 110 is placed in the vaginal cavity. The ejector tube 126 is then telescoped back into the outer tube 110 towards the distal end thereof (see FIG. 6), pushing the tampon 140 through the central opening 118 and spreading open the yieldable petal sections 114. Because of the unidirectional nature of the flaps 122, tampon 140 is free to move in the distal direction.

The forward extent of travel of the ejector tube 126 through the outer tube 110 is limited by the optional circumferential flange 136 which abuts against the proximal edge of the outer tube 110. Since the ejector tube 126 is preferably slightly longer than the outer tube 110, the distal end of the ejector tube 126 extends beyond the distal end of the outer tube 110. This ensures that the tampon 140 will be completely discharged into the vaginal cavity. Alternatively, the tube 126 may even be slightly shorter than the outer tube 110, to thus make the overall length of the assembled applicator 108 (with stored tampon 140) even more compact. In this latter case, it has been typically found that the vaginal muscles adequately grasp the tampon to ensure proper withdrawal of the applicator with the tampon remaining properly lodged in place.

The flaps 122 can also be used in a conventional telescoping tampon applicator (where the ejector tube is stored behind the tampon 40, which latter is stored directly in the distal end of the outer tube). The flaps 122b then serve to hold the distal end of the tampon 40 in position to back up the petals 14 and prevent pinching caused by slots 16.

I claim:

1. A catamenial tampon applicator comprising:
    an ejector tube adapted to store a tampon fitted therein with a small tip portion of said tampon extending from the distal end of said tube;
    an outer tube dimensioned to fit telescopically over said ejector tube and having a distal discharge end; and
    means fixed to the inside of the distal end of said outer tube and positioned at least closely adjacent a circumferentially continuous portion of said outer tube for gripping said extending portion of a tampon carried in said ejector tube so as to resist effectively proximal movement of such tampon relative to said outer tube during proximal withdrawal of the ejector tube over the tampon while permitting distal ejection of such tampon from the outer tube, said means being at least one flap dimensioned relative to said outer tube to extend substantially more in the circumferential direction than in the axial direction and to extend inwardly sufficiently to engage said extending distill tip portion of a tampon carried in said ejector tube, said flap being flexible in the axial direction and being canted in the distal direction.

2. A tampon applicator according to claim 1; further comprising circumferentially extending raised detent means and a mating circumferentially raised stopping means, one being formed on the outer distal surface of said ejector tube and the other being formed on the inner proximal end of said outer tube.

3. A catamenial tampon applicator according to claim 1; further comprising unidirectional restraining means for preventing the disassembly of said ejector tube from the proximal end of said outer tube, said restraining means including circumferentially extending raised detent means and a mating radially-overlapping circumferentially-extending stopping means respectively formed on the outer distal surface of said ejector tube and on the inner proximal end of said outer tube, said detent means having a proximal locking surface which is substantially perpendicular to the longitudinal axis of said applicator, said stopping means having a distal locking surface which is at least about 35° to said axis, said detent means having a distal sliding surface and said stopping means having a proximal sliding surface, which sliding surfaces are both cooperatively sloped at shallow enough angles relative to said axis to facilitate ease of assembly of said tubes.

4. A catamenial tampon applicator according to claim 3, wherein said detent means comprise a plurality of annularly extending ribs.

5. A catamenial tampon and applicator assembly comprising:
    a tampon applicator according to claim 1, in assembled form
    a tampon fitted within the distal end of said ejector tube with a small portion of said tampon extending from the distal end of said tube,
    the proximal end of said tampon having a concave configuration defining a peripheral ridge which is softer relative to the density of the remainder of said tampon.

6. A tampon applicator according to claim 1; in which said means include a plurality of inwardly directed flaps formed as part of said outer tube and which flaps arise from an inner distal surface of said outer tube.

7. A tampon applicator according to claim 6; in which there are at least three such inwardly directed flaps spaced and aligned at substantially equal intervals around the circumference of the inner surface of said outer tube.

8. A tampon applicator according to claim 7; in which said flaps are of a substantially flat blade-shape and are canted distally at an angle to the axis of said outer tube which ranges from 10° to 80°.

9. A catamenial tampon and applicator assembly comprising an applicator according to claim 7; wherein said tampon has a slightly enlarged head in the extending portion of the tampon with abrupt shoulders located distally adjacent said flaps.

10. A tampon applicator according to claim 8; in which said outer tube and said flaps are molded as a single unit from a plastic resin.

11. A tampon applicator according to claim 10; in which said ejector tube is formed from plastic.

12. A tampon applicator according to claim 11; in which the distal end of said ejector tube comprises a plurality of resilient undulations which are stiffly flexible with at least some of them being inwardly inclined to a diameter less than the diameter of the carried tampon at the distal end of the ejector tube, yet flexibly biased outwards by the carried tampon in a stored configuration and capable of passing over the tampon secured therein relative to the outer tube and then to spring back behind the tampon during partial withdrawal of the ejector tube.

13. A tampon applicator according to claim 10; in which all of said flaps are circumferentially aligned within 1/32 of an inch of the most distal end portion of the outer tube which is circumferentially continuous.

14. A tampon applicator according to claim 13, wherein said flaps have a circumferential width ranging from about 1/16 to ¼ of an inch.

15. A catamenial tampon and applicator assembly comprising an applicator according to claim 13; wherein said tampon has a slightly enlarged head in the extending portion of the tampon with abrupt shoulders located distally adjacent said flaps.

16. A tampon applicator according to claim 10; in which said distal end of said outer tube includes a plurality of petal sections which are shaped to form a substantially rounded tip and are sufficiently flexible to pass a tampon therethrough.

17. A tampon applicator according to claim 16; further including restraining means for preventing the disassembly of said ejector tube from said outer tube.

18. A tampon applicator according to claim 10; in which there is positive engaging means for displacing an effective portion of the distal end of said ejector tube inwardly behind the proximal end of said stored tampon when the ejector tube has been partially proximally withdrawn to a position entirely behind the proximal end of a stored tampon so as to insure positive engagement of the distal end of the tampon and thus prevent the tampon from reentering the ejector tube when the latter is distally pushed against the proximal end of the stored tampon to eject the tampon from the outer tube.

19. A tampon applicator according to claim 18; in which said distal end of said outer tube includes a plurality of petal sections which are shaped to form a substantially rounded tip and are sufficiently flexible to pass a tampon therethrough.

20. A tampon applicator according to claim 19; further including restraining means for preventing the disassembly of said ejector tube from said outer tube.

21. A tampon applicator according to claim 20; in which the distal end of said ejector tube comprises a plurality of resilient undulations.

22. A catamenial tampon applicator according to claim 20; further comprising unidirectional restraining means for preventing the disassembly of said ejector tube from the proximal end of said outer tube, said restraining means including circumferentially extending raised detent means and a mating radially-overlapping circumferentially-extending stopping means respectively formed on the out distal surface of said ejector tube and on the inner proximal end of said outer tube, said detent means having a proximal locking surface which is substantially perpendicular to the longitudinal axis of said applicator, said stopping means having a distal locking surface which is at least about 35° to said axis, said detent means having a distal sliding surface and said stopping means having a proximal sliding surface, which sliding surfaces are both cooperatively sloped at shallow enough angles relative to said axis to facilitate ease of assembly of said tubes.

23. A catamenial tampon and applicator assembly comprising an applicator according to claim 20; wherein said tampon has a slightly enlarged head in the extending portion of the tampon with abrupt shoulders located distally adjacent said flaps.

24. A catamenial tampon and applicator assembly according to claim 23; wherein said enlarged head is shaped to underlie and support said petal sections.

25. A catamenial tampon and applicator assembly comprising:
a tampon applicator according to claim 1 in assembled form,
said outer tube being telescopically collapsed over said ejector tube such that the flaps of said outer tube engage the extending portion of said tampon,
said tampon being fitted within the distal end of said ejector tube with a small portion of said tampon extending from the distal end of said ejector tube,
said ejector tube being formed of plastic and having a plurality of resiliant undulations at its distal end which are stiffly flexible and which have portions inwardly inclined to a reduced diameter sufficient to assure the capability of effective positive engagement of the proximal end of said tampon when said ejector tube has been withdrawn in the proximal direction to be positioned behind the tampon in an expulsion configuration,
said tampon having an accommodation diameter at least near its distal end to accommodate said undulations, which accommodation diameter is sufficiently smaller than the tail diameter at the proximal end of said tampon to assure maintenance over time of said effective positive engagement capability.

26. A catamenial tampon and applicator assembly according to claim 25, wherein the difference between said accommodation diameter and the proximal diameter of said tampon is between about 0.005 to about 0.030 inches.

27. A catamenial tampon and applicator assembly according to claim 25, wherein the majority of said tampon from said accommodation diameter up to the proximal end of said tampon is of the same smaller diameter.

28. A catamenial tampon and applicator assembly according to claim 27, wherein the extending portion of said tampon has an enlarged head located distally adjacent said flaps with abrupt shoulders narrowed down to said accommodation diameter to engage said flaps and also to engage proximally adjacent to said flaps the ends of the inwardly directed portions of said undulations.

29. A tampon applicator according to claim 8, wherein said flaps each have a linear tip portion which is serrated.

* * * * *